United States Patent
Kumar et al.

(10) Patent No.: US 10,436,721 B2
(45) Date of Patent: Oct. 8, 2019

(54) X-RAY IMAGING AND CHEMICAL ANALYSIS OF PLANT ROOTS

(71) Applicant: UHV Technologies, Inc., Fort Worth, TX (US)

(72) Inventors: Nalin Kumar, Fort Worth, TX (US); Manuel Gerardo Garcia, Lexington, KY (US)

(73) Assignee: UHV Technologies, Inc., Fort Worth, TX (US)

(*) Notice: Subject to any disclaimer, the term of this patent is extended or adjusted under 35 U.S.C. 154(b) by 449 days.

(21) Appl. No.: 15/217,011

(22) Filed: Jul. 22, 2016

(65) Prior Publication Data

US 2017/0031053 A1   Feb. 2, 2017

Related U.S. Application Data

(60) Provisional application No. 62/195,635, filed on Jul. 22, 2015.

(51) Int. Cl.
*G01N 23/046* (2018.01)
*G01N 23/223* (2006.01)
*G01V 5/00* (2006.01)

(52) U.S. Cl.
CPC ......... *G01N 23/046* (2013.01); *G01N 23/223* (2013.01); *G01V 5/005* (2013.01); *G01V 5/0016* (2013.01)

(58) Field of Classification Search
CPC ...... A61B 6/032; A61B 6/035; G01N 23/046; G01V 5/0016; G01V 5/005
USPC .............................. 378/9, 10, 53, 57, 19, 62
See application file for complete search history.

(56) References Cited

U.S. PATENT DOCUMENTS

| | | | |
|---|---|---|---|
| 4,283,629 A | 8/1981 | Habermehl et al. | |
| 6,088,423 A * | 7/2000 | Krug | G01V 5/0041 378/4 |
| 6,236,709 B1 * | 5/2001 | Perry | G01N 23/046 378/25 |
| 6,453,003 B1 * | 9/2002 | Springer | G01N 23/06 378/51 |

(Continued)

FOREIGN PATENT DOCUMENTS

| | | |
|---|---|---|
| EP | 1546335 A4 | 8/2005 |
| WO | 2006/114714 | 11/2006 |

(Continued)

OTHER PUBLICATIONS

International Searching Authority, International Preliminary Report on Patentability, International Application No. PCT/US2016/043526, dated Feb. 1, 2018.

(Continued)

*Primary Examiner* — Allen C. Ho
(74) *Attorney, Agent, or Firm* — Kelly Kordzik; Matheson Keys & Kordzik PLLC

(57) ABSTRACT

A linear x-ray tube having one or more x-ray sources is configured for insertion into the soil in proximity to a root system of a plant for emission of an x-ray beam detected by a linear array of one or more x-ray detectors. The linear x-ray tube and detector array may be inserted into rhizotrons previously inserted into the soil. Various combinations of multiple x-ray tubes and/or detector arrays may be utilized to customize the x-ray imaging of the root system.

20 Claims, 16 Drawing Sheets

(56) References Cited

U.S. PATENT DOCUMENTS

| | | | | |
|---|---|---|---|---|
| 6,473,487 | B1* | 10/2002 | Le | G01N 23/04 378/57 |
| 6,597,760 | B2* | 7/2003 | Beneke | G01V 5/0016 378/57 |
| 7,020,241 | B2* | 3/2006 | Beneke | G01V 5/0016 378/54 |
| 7,082,182 | B2* | 7/2006 | Zhou | A61B 6/032 378/10 |
| 7,103,137 | B2* | 9/2006 | Seppi | G01N 23/04 378/57 |
| 7,103,138 | B2* | 9/2006 | Pelc | A61B 6/032 378/4 |
| 7,215,737 | B2* | 5/2007 | Li | G01V 5/0016 378/57 |
| 7,227,923 | B2* | 6/2007 | Edic | A61B 6/032 378/115 |
| 7,233,644 | B1* | 6/2007 | Bendahan | G01N 23/046 378/57 |
| 7,278,236 | B2* | 10/2007 | McDonald | A01G 7/00 47/1.01 R |
| 7,280,631 | B2* | 10/2007 | De Man | A61B 6/032 378/10 |
| 7,295,651 | B2* | 11/2007 | Delgado | G01N 23/046 378/10 |
| 7,400,701 | B1* | 7/2008 | Cason | G01V 5/0025 378/57 |
| 7,428,297 | B2* | 9/2008 | Eilbert | G01N 23/2252 378/10 |
| 7,526,064 | B2* | 4/2009 | Akery | G01N 23/04 378/198 |
| 7,606,348 | B2* | 10/2009 | Foland | G01N 23/046 378/4 |
| 7,616,731 | B2* | 11/2009 | Pack | G01N 23/046 378/10 |
| 7,706,499 | B2* | 4/2010 | Pack | A61B 6/027 378/10 |
| 7,813,478 | B2* | 10/2010 | Nisius | G01V 5/0041 378/115 |
| 7,826,594 | B2* | 11/2010 | Zou | H01J 1/30 378/10 |
| 7,831,012 | B2* | 11/2010 | Foland | G01N 23/04 378/57 |
| 7,835,486 | B2* | 11/2010 | Basu | A61B 6/027 378/10 |
| 7,864,917 | B2* | 1/2011 | Ribbing | A61B 6/032 378/10 |
| 7,874,730 | B2* | 1/2011 | Harding | G01N 23/20083 378/207 |
| 7,903,789 | B2 | 3/2011 | Morton et al. | |
| 8,300,763 | B2* | 10/2012 | Shedlock | G01N 23/046 378/57 |
| 8,391,550 | B2* | 3/2013 | Pachys | G01N 23/046 382/103 |
| 8,594,272 | B2* | 11/2013 | Funk | A61B 6/032 378/10 |
| 8,774,351 | B2* | 7/2014 | Funk | A61B 6/4488 378/62 |
| 8,971,484 | B2* | 3/2015 | Beckmann | G01V 5/005 378/122 |
| 9,046,465 | B2* | 6/2015 | Thompson | G01N 23/04 |
| 9,330,493 | B2* | 5/2016 | Schajer | G01N 23/046 |
| 9,380,990 | B2* | 7/2016 | Kim | A61B 6/502 |
| 9,460,823 | B2* | 10/2016 | Song | H05K 7/2039 |
| 9,658,201 | B2* | 5/2017 | Redden | G01N 33/0098 |
| 9,778,391 | B2* | 10/2017 | Chen | G01V 5/0016 |
| 9,816,948 | B2* | 11/2017 | Haidekker | G01N 33/025 |
| 9,867,582 | B2* | 1/2018 | Kim | A61B 6/08 |
| 10,207,296 | B2* | 2/2019 | Garcia | B07C 5/3416 |
| 2006/0207172 | A1 | 9/2006 | McDonald et al. | |
| 2015/0015697 | A1 | 1/2015 | Redden et al. | |
| 2015/0049855 | A1 | 2/2015 | Funk et al. | |
| 2015/0324975 | A1 | 11/2015 | Cope et al. | |

FOREIGN PATENT DOCUMENTS

| | | |
|---|---|---|
| WO | 2009/042671 | 4/2009 |
| WO | 2014/100237 | 6/2014 |

OTHER PUBLICATIONS

S.N. Johnson et al., "Non-invasive techniques for investigating and modeling root-feeding insects in managed and natural systems," Agricultural and Forest Entomology, vol. 9, Issue 1, Oct. 31, 2006, pp. 39-46.

International Searching Authority, International Search Report and the Written Opinion, International Application No. PCT/US2016/043526, dated Nov. 7, 2016.

Heeraman et al., "Three dimensional imaging of plant roots in situ with X-ray Computed Tomography," Plant and Soil, vol. 189, Feb. 1997, pp. 167-179.

Himmelbauer et al., "Estimating length, average diameter and surface area of roots using two different Image analyses systems," Plant and Soil, vol. 260, Mar. 2004, pp. 111-120.

Iversen et al., "Advancing the use of minirhizotrons in wetlands," Plant Soil, vol. 352, issue 1-2, pp. 23-39, Sep. 10, 2011.

Johnson et al., "Advancing fine root research with minirhizotrons," Environmental and Experimental Botany, vol. 45, issue 3, pp. 263-289, Apr. 19, 2001.

Mairhofer et al., "RooTrak: Automated Recovery of Three-Dimensional Plant Root Architecture in Soil from X-Ray Microcomputed Tomography Images Using Visual Tracking," Plant Physiology, vol. 158, pp. 561-569, Feb. 2012.

Page et al., "Novel X-ray imaging and segmentation of root structures," Sensor Review, vol. 28, No. 1, pp. 46-51, 2008.

Rousseau et al., "Multiscale imaging of plants: current approaches and challenges," Plant Methods, 11:6, 9 pages, Feb. 10, 2015.

Seignez et al., "Development of Plant Roots Network in Polluted Soils: An X-ray Computed Microtomography Investigation," Water Air Soil Pollut., vol. 209, issue 1-4, pp. 199-207, Oct. 16, 2009.

* cited by examiner

X-RAY IMAGING AND CHEMICAL ANALYSIS OF PLANT ROOTS

This patent application claims priority to U.S. provisional patent application Ser. No. 62/195,635, which is hereby incorporated by reference herein.

GOVERNMENT LICENSE RIGHTS

This invention was made with U.S. government support under Grant No. DE-AR0000422 awarded by the U.S. Department of Energy. The U.S. government may have certain rights in this invention.

TECHNOLOGY FIELD

The present disclosure relates in general to the agricultural field, and in particular, to the imaging and chemical characterization of plant roots.

BACKGROUND INFORMATION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

The root structures of plants are an unseen part of plant physiology. To image and observe plant roots, several methods have been developed. One such method involves removing the plant and its surrounding soil out of the container in which it was growing, washing the soil from the plant roots, and imaging the roots using a desktop flatbed scanner. Another method for imaging plant roots is performed using devices called rhizotrons. These are transparent tubes that are placed in the ground. After plant roots grow around the rhizotron, a visible light camera is placed in the tube for capturing images of the plant roots that are on the external surface of the rhizotron. For example, see M. G. Johnson et al., "Advancing fine root research with minirhizotrons," Environmental and Experimental Botany, vol. 45, issue 3, pp. 263-289, Apr. 19, 2001; and C. M. Iversen et al., "Advancing the use of minirhizotrons in wetlands," Plant Soil, vol. 352, issue 1-2, pp. 23-39, Sep. 10, 2011. These methods are glass-wall techniques where the plant roots are visually observed at the wall-soil boundary. Unfortunately, most plant roots are still not visible since a vast majority of the plant roots are not near the glass wall, and the visible cameras cannot see through the soil.

Thus, there is a need to develop technologies to image plant root phenotypes in situ. Currently no technologies exist that have been designed to image plant roots in complex media, such as agricultural field conditions. Even the best existing imaging modalities such as x-ray, MRI, and PET have limitations when imaging different components of complex media, such as soil containing plant roots, minerals, and rocks. Furthermore, none of these technologies are currently deployable in open agricultural fields.

Further information on imaging of plant roots can be found in the following publications, all of which are hereby incorporated by reference herein: N. Seignez et al., "Development of Plant Roots Network in Polluted Soils: An X-ray Computed Microtomography Investigation," Water Air Soil Pollut., vol. 209, issue 1-4, pp. 199-207, Oct. 16, 2009; and D. Page et al., "Novel X-ray imaging and segmentation of root structures," Sensor Review, vol. 28, no. 1, pp. 46-51, 2008.

It should be noted that D. Page et al. did not utilize a linear x-ray tube, and their system required a low density, low-attenuation substrate to serve as an artificial medium to support the plant roots, meaning that their system could not use x-ray imaging of plant roots as planted in their native soil.

DETAILED DESCRIPTION

Figure 1:
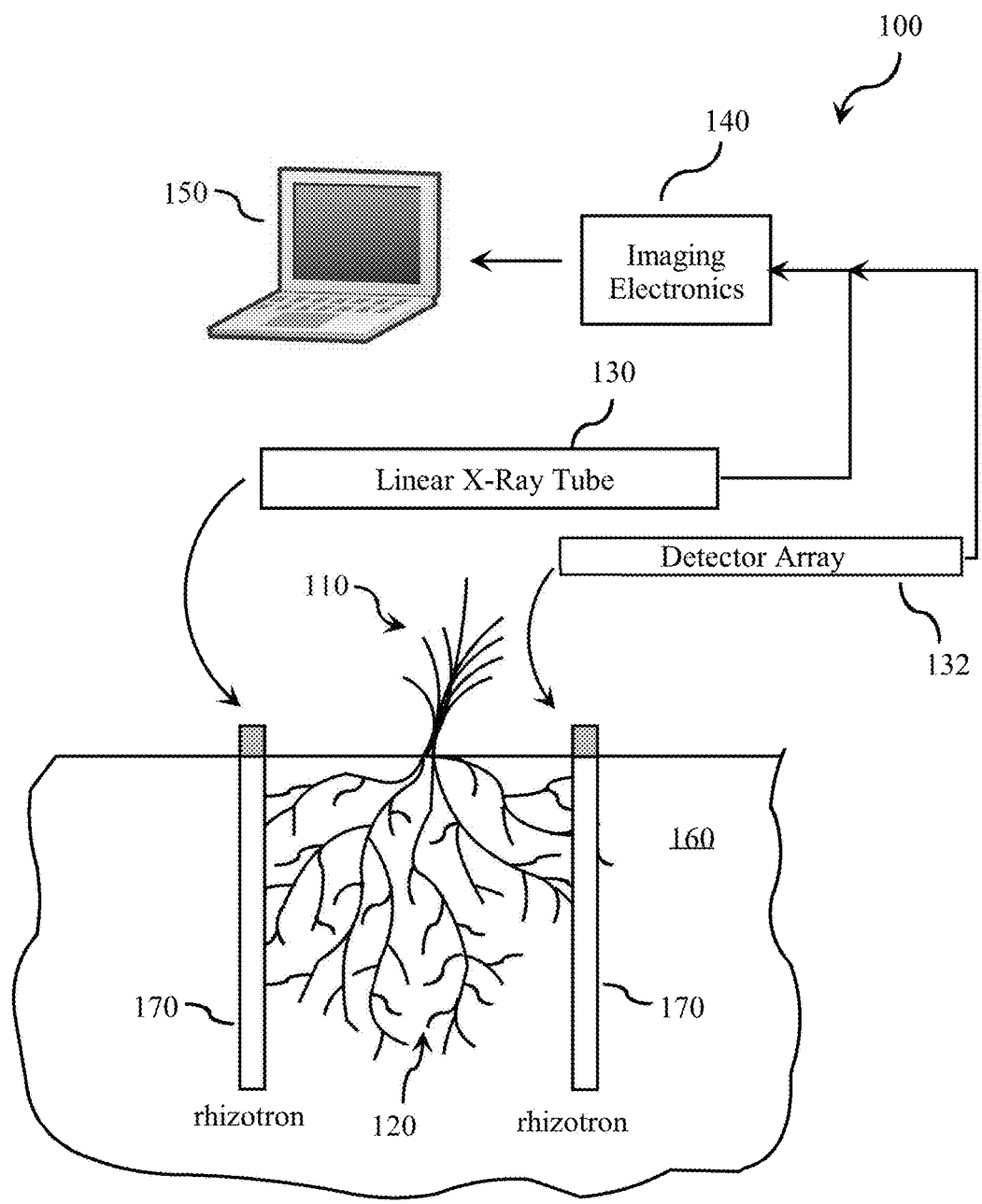
FIG. 1 illustrates a plant root characterization system according to embodiments of the present invention.

Aspects of the present disclosure provide an innovative system for characterizing various physical and chemical properties of plant root systems, including those growing within their native soil environment (e.g., within an agriculture field), which utilizes a linear x-ray tube as disclosed in U.S. patent application Ser. No. 15/213,129, now U.S. Pat. No. 10,207,296 B2 issued on Feb. 19, 2019, which is hereby incorporated by reference herein. As used herein, the term "native soil" refers to the ground located in a natural habitat in which a plant has grown, which may be an agriculture field in which the plant has been grown as an agriculture crop.

Aspects of the present disclosure provide an innovative x-ray root imaging system, which may be utilized for phytosequestration experimentation and data gathering.

Aspects of the present disclosure provide a low cost, stationary, three-dimensional ("3D") x-ray computed tomography ("CT") system with sophisticated reconstruction and image segmentation algorithms, which can image total root phenotypes in situ. X-ray CT is an imaging procedure that utilizes computer-processed x-rays to produce tomographic images or "slices" of an object. X-ray slice data is generated using an x-ray imaging system that includes an x-ray source or generator and an image detection system, which can be either a film (analog technology) or a digital capture system. Aspects of the present invention provide a novel, non-destructive, field-deployable technology to perform imaging of hundreds of plants per cycle to correlate phenotypes to genetic markers, which has the characteristics of small size, high resolution, and fast imaging of fine plant roots. Aspects of the present invention provide a low power consumption and easy to field deploy CT system that greatly increases the speed and efficacy of discovery, field translation, and deployment of improved crops and systems that improve soil carbon accumulation and storage, decrease $N_2O$ emissions, and improve water efficiency leading towards advancements that can mitigate up to 10% of the total U.S. greenhouse gases.

Aspects of the present invention provide an x-ray CT system that outputs high resolution images of plant roots in situ, with a fast acquisition time and large penetration depth (i.e., ability to image plant roots through several feet of soil). Prior art optical systems cannot see through the soil, and are limited to imaging only those plant roots that physically touch the walls of a transparent rhizotron. In contrast, aspects of the present invention are configured to measure plant root mass in a non-destructive, non-invasive fashion in the field, including acquisition of high resolution 3D data at a throughput of hundreds of plants per cycle.

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description is not intended to limit the scope of the invention, as claimed, but is presented for purposes of illustration only to describe the features and characteristics of the present invention, to set forth the best mode of operation of the invention, and to sufficiently enable one skilled in the art to practice the invention. Accordingly, the scope of the present invention is to be defined solely by the appended claims.

FIG. 1 illustrates embodiments of a plant root characterization system 100 for characterizing the root system 120 of a plant 110. The plant root characterization system 100 includes a radiation source 130, a detector array 132, an image capture system 140, and an image processing system 150. The plant root characterization system 100 operates by passing radiation, such as x-rays, through the soil 160 in which the root system 120 of the plant 110 is growing. The detector array 132 captures the radiation passing through the root system 120 and sends information pertaining to the detected radiation to the image capture system 140 to form an image of the root system 120. The image processing system 150 may operate on the captured image(s) to enhance its visual quality and extract useful characteristics of its structure and growth.

In embodiments of the present invention, the radiation source 130 is a linear x-ray tube with one or more x-ray sources, such as described herein with respect to FIGS. 9-13. In embodiments of the present invention, the detector array 132 may include one or more M (M≥1) well-known x-ray detectors, which may be linearly aligned within the detector array 132.

Figure 6:
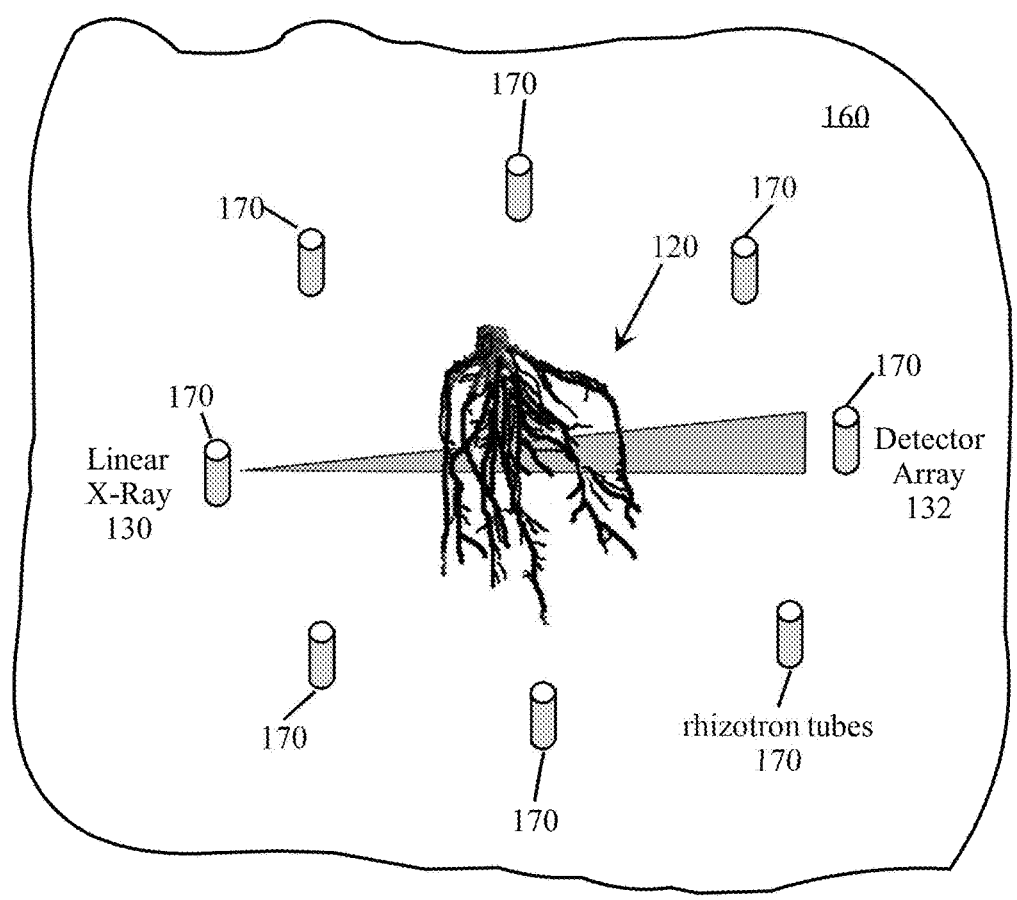
FIG. 6 schematically illustrates an example of a linear x-ray tube and detector array inserted in multiple rhizotrons utilized for imaging a plant root system.
Figure 7:
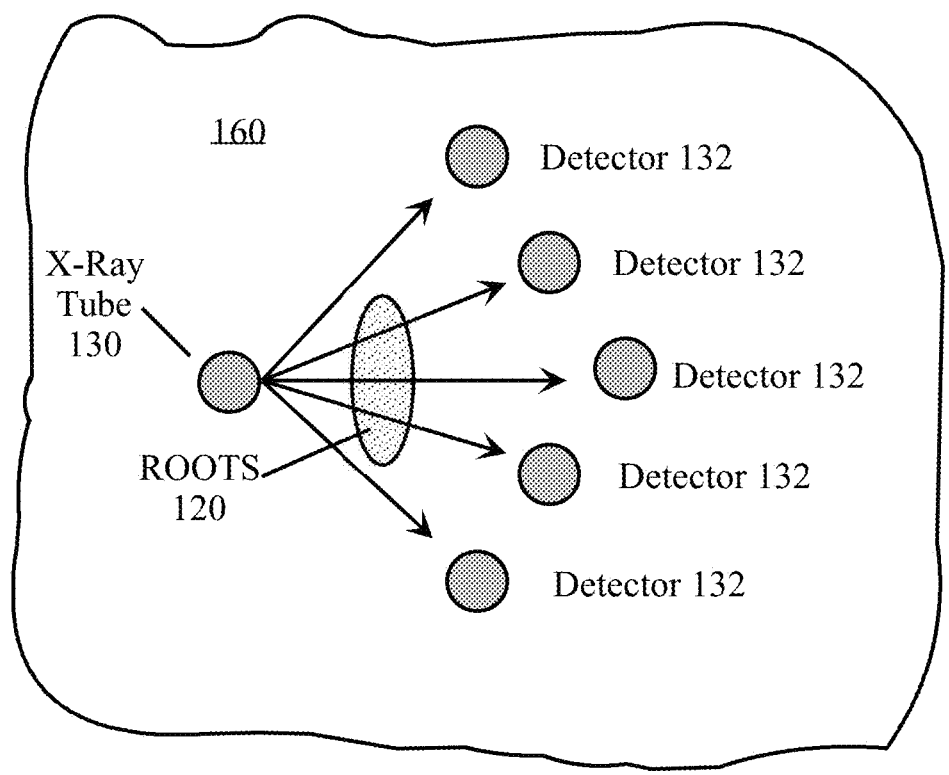
FIG. 7 illustrates embodiments of the present invention in which multiple arrays of detectors may be arranged in relationship to a linear x-ray tube.
Figure 8:
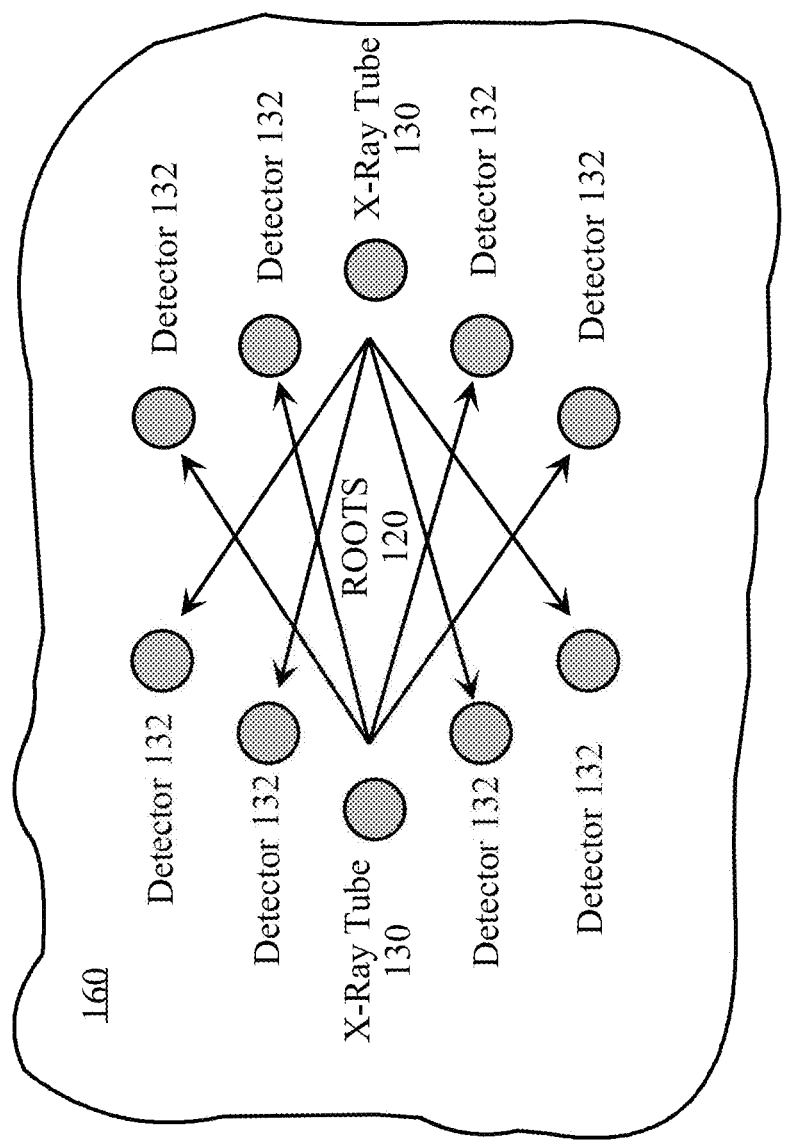
FIG. 8 illustrates embodiments in which multiple linear x-ray tubes may be positioned in relation to multiple detector arrays.

In embodiments of the present invention, one or more such linear x-ray tubes 130 may be configured to be inserted directly into the soil 160, or fit within rhizotron(s) 170 that have been inserted into the soil 160 in specified location(s) in proximity to the root system 120 (e.g., see FIGS. 6 and 8). Likewise, one or more detector arrays 132 may be configured to be inserted directly into the soil 160, or fit within rhizotron(s) 170 that have been inserted into the soil 160 in specified location(s) in proximity to the root system 120 (e.g., see FIGS. 6-8). The linear x-ray tube(s) 130 and detector array(s) 132 may be configured to perform x-ray computed tomography ("CT").

The image capture system 140 may be configured to capture one image at a time of all or a portion of a root system 120 for characterization of that portion. Or, the image capture system 140 may be configured to capture multiple images used to form a tomographic reconstruction or photomontage.

The image processing system 150 receives the image(s) from the image capture system 140 and may process the image(s) to enhance the contrast between the roots of the root system 120 and the surrounding soil 160. Embodiments of the image processing system 150 may include software that performs a density computation process based at least in part on a comparison to the localized density of a reference material.

The image processing system 150 may include software for reconstructing the architecture of the plant root system 120 from the x-ray CT images, such as the RootViz3D software tool commercially available from Davidson's Agricultural Research and Development, or RooTrak, which is an open-source tool developed to aid in the separation process of plant roots from the surrounding soil 160, in x-ray micro-computed tomography ("μCT") images. The RooTrak tool facilitates the extraction and visualization of plant root systems 120 and allows the quantification of certain root system traits. RooTrak is commercially available for download from SourceForge. The RooTrak tool is further described in S. Mairhofer et al., "RooTrak: Automated Recovery of Three-Dimensional Plant Root Architecture in Soil from X-Ray Microcomputed Tomography Images Using Visual Tracking," Plant Physiology, vol. 158, pp. 561-569, February 2012, which is hereby incorporate by reference herein.

The plant root characterization system 100 may be transported to the site of the plant 110 (e.g., an agriculture field in which the plant 110 has been planted in native soil) (e.g., see FIG. 15), or the plant 110 may be transported to the plant root characterization system 100 (e.g., in a diagnostic laboratory).

Figure 2:
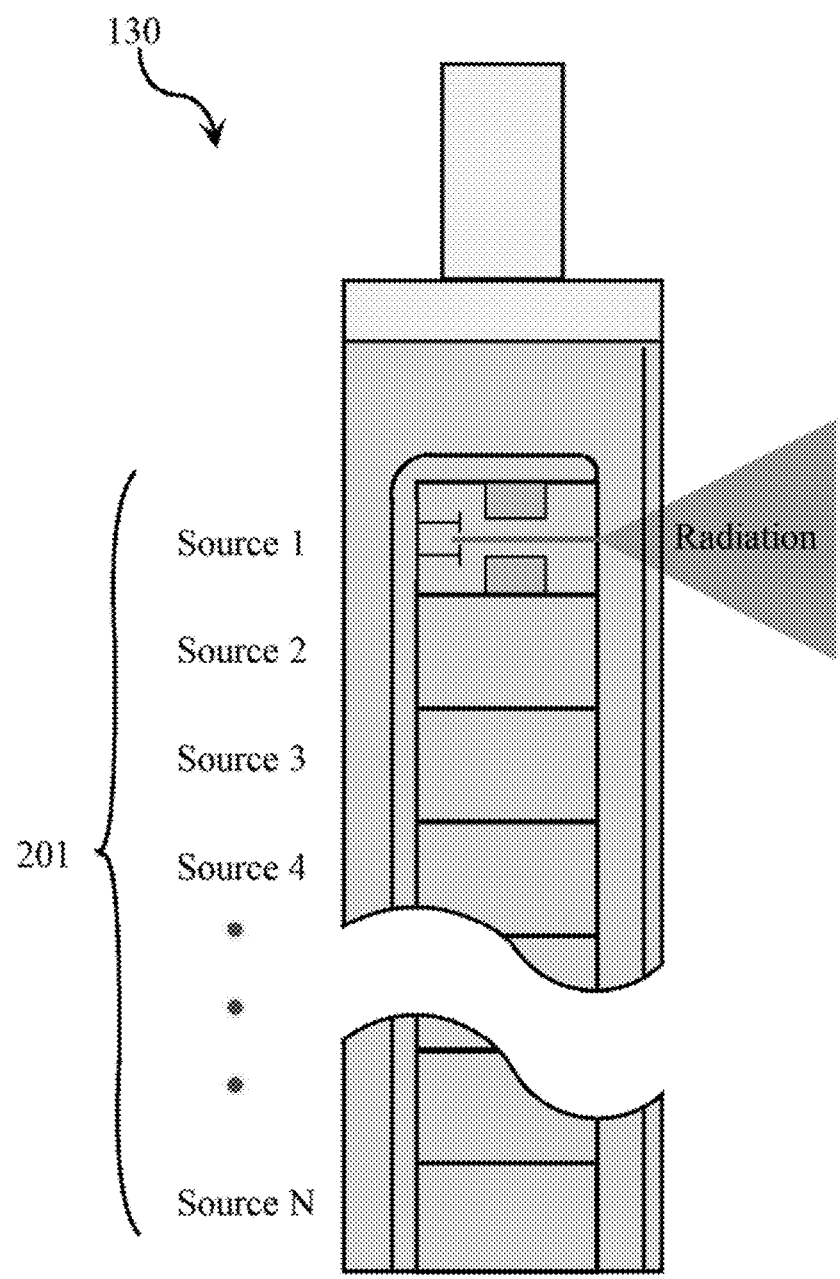
FIG. 2 illustrates a linear x-ray tube, configured in accordance with embodiments of the present invention, containing one or more individually-controlled x-ray sources.
Figure 3:
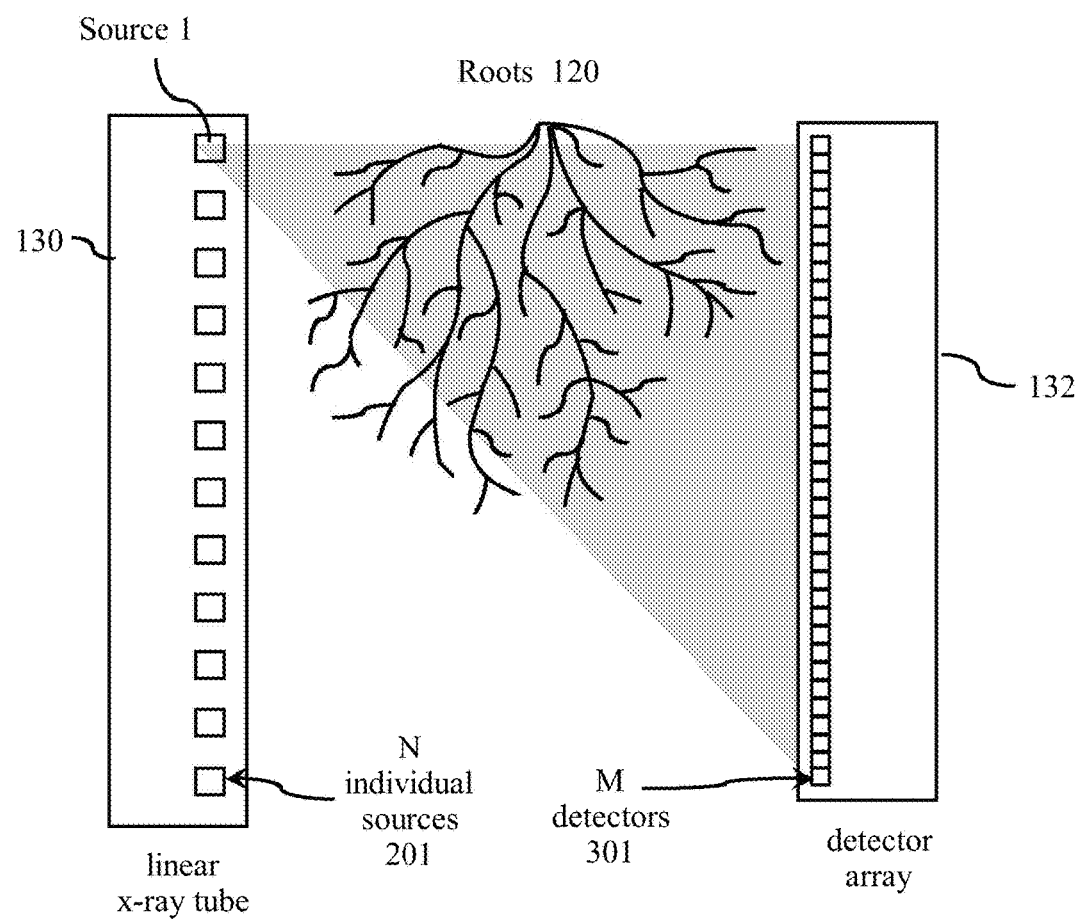
FIGS. 3, 4 and 5 schematically illustrate examples of multiple x-ray sources within a linear x-ray tube and multiple detectors within a detector array configured for imaging a plant root system in accordance with embodiments of the present invention.
Figure 4:
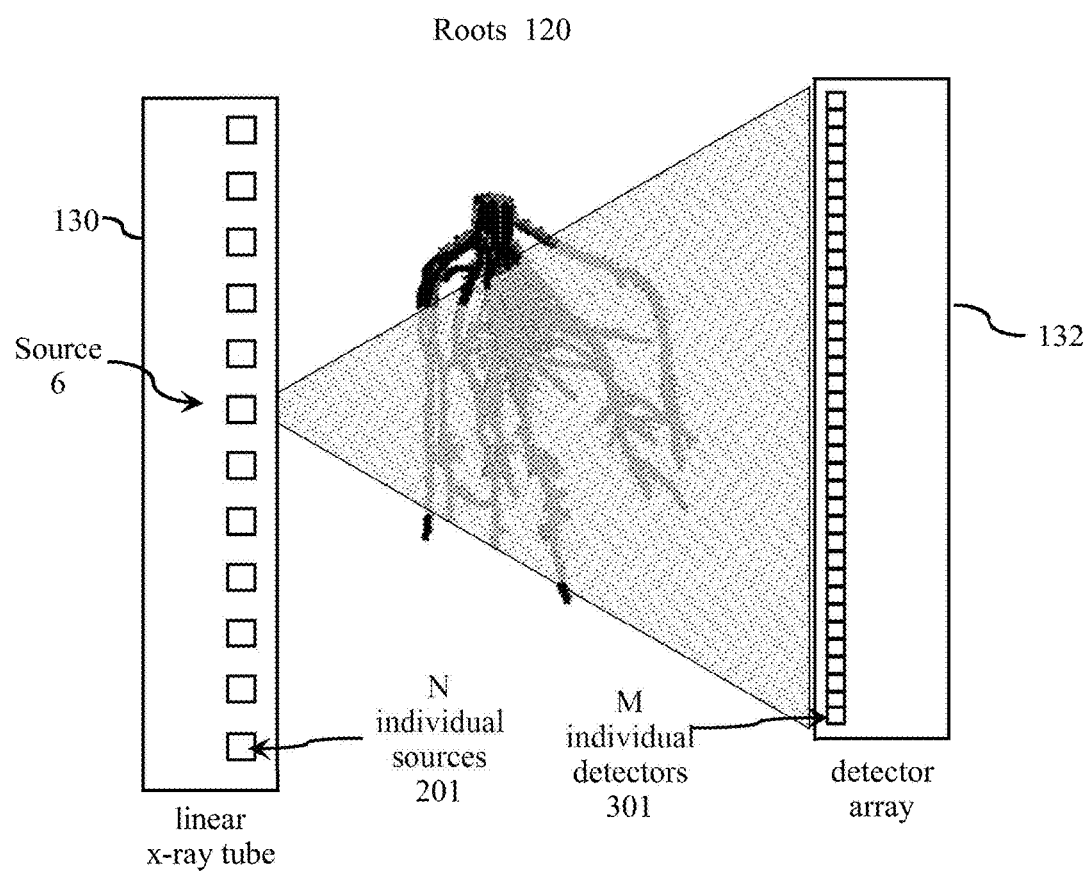
Figure 5:
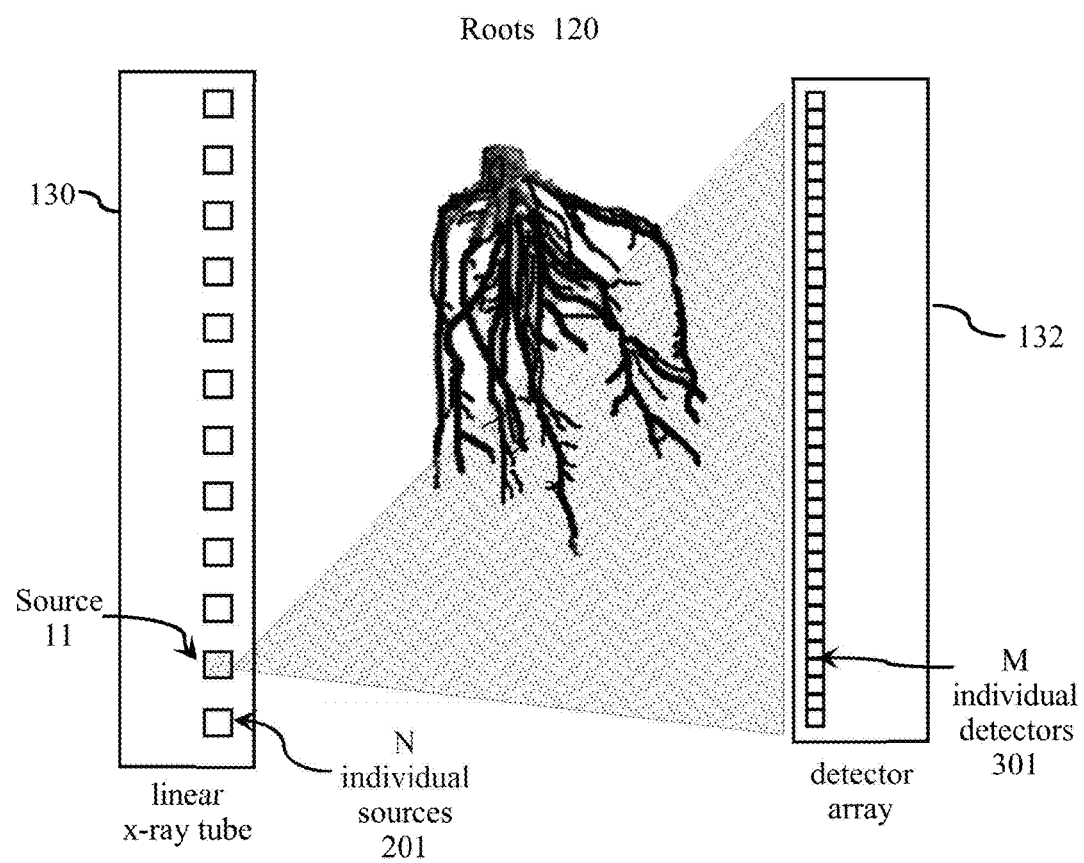

FIG. 2 illustrates a linear x-ray tube 130, configured in accordance with embodiments of the present invention, containing one or more individually-controlled x-ray sources. The linear x-ray tube 130 may include one or more N (N≥1) individual x-ray sources 201 whereby each of the N x-ray sources 201 is configured to emit an x-ray beam (radiation) (e.g., through a medium (e.g., the soil 160)) containing a plant root system 120 (i.e., the plant roots) and towards a detector array 132 of one or more M detectors. As can be seen in FIGS. 3-5, portions of each radiation beam may be detected by one or more of the M detectors in a particular detector array 132.

Referring again to FIG. 2, each linear x-ray tube 130 may be configured with N x-ray sources 201, wherein each of the N x-ray sources 201 may be individually and separately controlled by the plant root characterization system 100 in any manner desired so as to produce any combination of images of any one or more portions of the root system 120.

For example, referring to FIG. 3, there is schematically illustrated an embodiment where a first one of the N x-ray sources 201 (labeled as "N individual sources 201" in FIG. 3) (e.g., Source 1) is activated to emit an x-ray beam, which passes through at least a portion of the root system 120 (labeled as "Roots 120" in FIG. 3) for detection by one or more of the M individual detectors 301 within the detector array 132. FIG. 4 schematically illustrates an exemplary embodiment where another one of the N x-ray sources 201 (labeled as "N individual sources 201" in FIG. 4) (e.g., Source 6) is activated to emit an x-ray beam that passes through at least a portion of the root system 120 (labeled as "Roots 120" in FIG. 4) to be detected by one or more of the M individual detectors 301 within the detector array 132. In a like manner, FIG. 5 schematically illustrates an exemplary embodiment whereby another one of the N x-ray sources 201 (labeled as "N individual sources 201" in FIG. 5) (e.g., Source 11) is activated to emit an x-ray beam that passes through at least a portion of the root system 120 (labeled as "Roots 120" in FIG. 5) for detection by one or more of the M individual detectors 301 within the detector array 132.

Each of the M individual detectors 301 within the detector array 132 may be a well-known x-ray detector configured to detect certain wavelengths of the x-ray beam, including all of the M individual detectors 301 configured to detect the same wavelength(s) of the emitted x-ray beam.

As a result, it can be readily seen by one of ordinary skill in the art that imaging of the root system 120 may be performed by embodiments of the present invention in a manner so that any one or more of the N x-ray sources 201 may be activated in any desired combination to emit their respective x-ray beams through any desired portion, or portions, of the root system 120 for detection by any desired combination of the M individual detectors 301 in the detector array 132. As shown in FIGS. 3-5, when used with such a detector array 132, the N x-ray sources 201 of one or more linear x-ray tubes 130 can be individually activated/deactivated (e.g., in sequence) to produce a 3D image of the root system 120.

FIG. 6 schematically illustrates further exemplary embodiments of the present invention in which a plurality of rhizotrons 170 have been inserted into the soil 160 surrounding at least a portion of a root system 120. The placement of the rhizotrons 170 in the soil 160 may be performed in any desired arrangement, and include any number of such rhizotrons 170. FIG. 6 schematically illustrates an exemplary embodiment in which a linear x-ray tube 130 (labeled as "Linear X-Ray 130" in FIG. 6) has been inserted into one of the rhizotrons 170, while a detector array 132 has been inserted into one of the other rhizotrons 170. This can be performed in any desired combination, as shown in FIGS. 7-8.

FIG. 7 depicts embodiments of the present invention in which multiple detector arrays 132 may be arranged in relationship to a linear x-ray tube 130 (labeled as "X-Ray Tube 130" in FIG. 7). The depiction of FIG. 7 is shown from the top looking down onto the medium (e.g., soil 160) containing the root system 120 (labeled as "ROOTS 120" in FIG. 7), so that only the ends of the linear x-ray tube 130 and the detector arrays 132 are shown (e.g., such as inserted within rhizotrons 170).

FIG. 8 is similar to FIG. 7, except for depicting embodiments in which two or more multiple linear x-ray tubes 130 teach labeled as "X-Ray Tube 130" in FIG. 8) may be positioned in relation to one or more detector arrays 132.

The arrows in FIGS. 7-8 depict possible pathways and combinations of pathways of emitted x-ray beams.

As can be seen with respect to FIGS. 3-8, the linear x-ray tube 130 contains a plurality of individually-controlled x-ray sources 201 in one low-cost package, enabling CT imaging of the plant roots of the root system 120 without the need to move x-ray sources 201.

Attributes of the linear x-ray tube 130 include electronically controlled point sources, no limit to number of point sources, one and two dimensional arrays of point sources, adjustable dose and energy to enhance contrast, sub-micron imaging resolution, depth of imaging >6 feet, with a tube length that is variable.

Referring to FIGS. 9-13, the linear x-ray tube 130 may be configured in a manner similarly to the linear x-ray tube 900, which may be configured with N (N≥1) separate x-ray sources (pertaining to the x-ray sources 201), wherein the linear x-ray tube 900 is configured so that each of the N x-ray sources can be independently controlled. Though the linear x-ray tube 900 is described herein having four x-ray sources 910, 911, 912, 913 linearly aligned adjacent to each other within the linear x-ray tube 900, such a linear x-ray tube may be configured with any number N (N≥1) of such x-ray sources. Such a linear x-ray tube 900 having multiple sources instead of one each operable at a relatively low power, significantly reduces the cost and power requirements versus having to utilize multiple separately powered x-ray sources.

Referring to FIGS. 9-12, a linear x-ray tube 900 includes an anode assembly 960, N cathode materials 990, and a grid assembly 939, positioned inside of a vacuum package 901. The anode assembly 960 may be composed of a conductive (e.g., copper) bar mechanically attached to a high voltage feed-through 921. This bar may substantially span a length of the linear x-ray tube 900. Alternatively, the anode assembly 960 may be a plurality (e.g., N) of separate conductive bars connected in series. Several different coatings may be added to the copper bar 960, including, molybdenum, tungsten, silver, or any metal. This metal or combinations of metals can then be brazed onto the copper bar 960 in order to provide a layer that will generate the desired x-ray spectrum. Different metals will generate different output spectra from the linear x-ray tube 900. In addition to brazing, these metals may be mechanically attached to the bar 960. The bar 960 may also be composed of any metal other than copper. The high voltage feed-through 921 transfers a high voltage from the external environment of the linear x-ray tube 900 to the inside of the linear x-ray tube 900. The anode assembly 960 and all the materials it comes into contact may be held at this high voltage (e.g., 0-500 kV).

Figure 9:
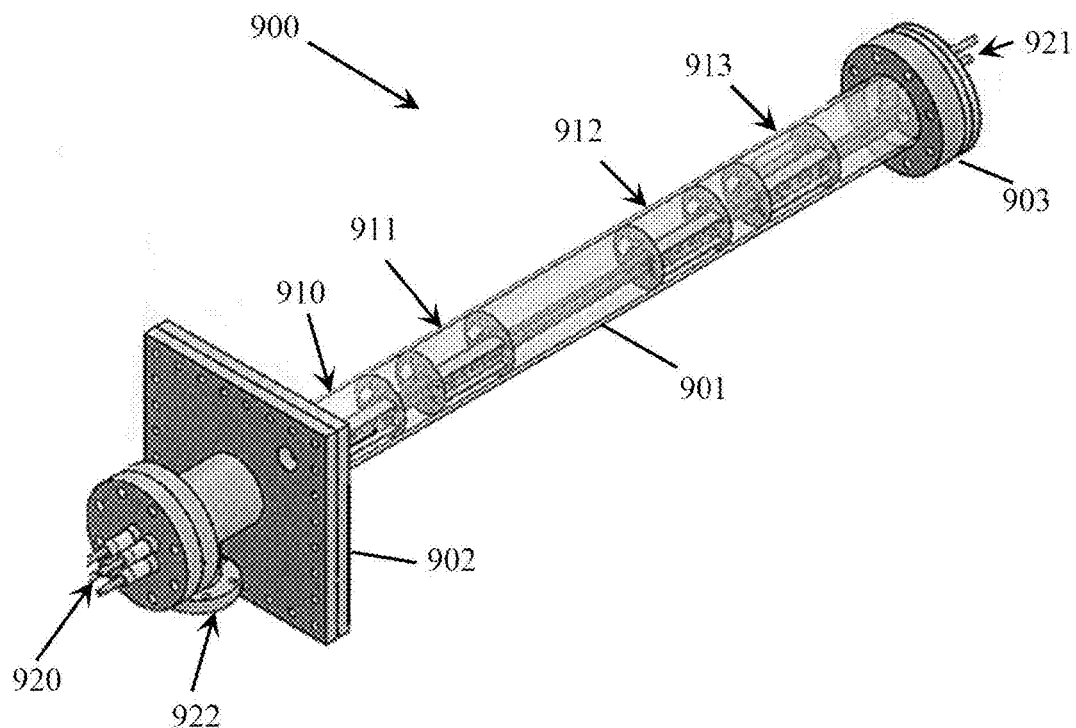
FIGS. 9, 10, 11, 12 and 13 illustrate an exemplary linear x-ray tube configured in accordance with embodiments of the present invention.
Figure 10:
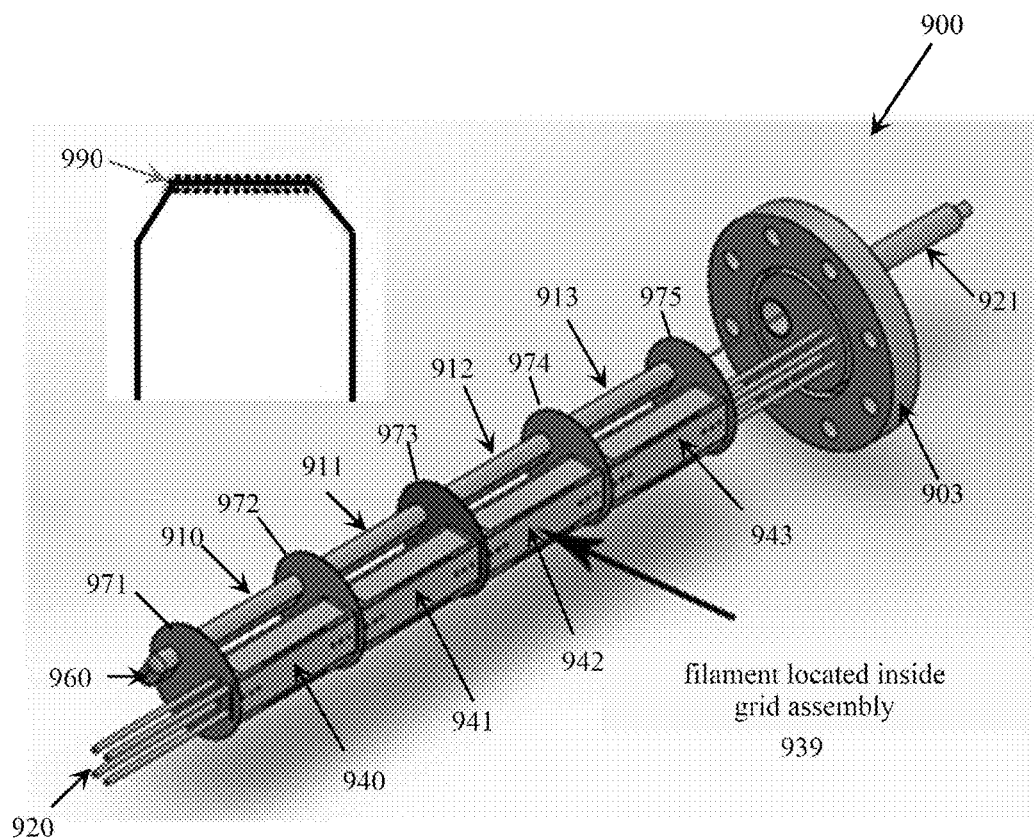

A purpose of the N cathode materials 990 (see inset of FIG. 10) is to emit electrons. The N cathode materials 990 may be made of tungsten, but may also be thoriated tungsten, an oxide cathode, a cold cathode, or any electron emitter. The tungsten filaments may be wound into a spiral shape in order to increase the electron emission density for the volume of the spiral section of the filament shape. The two ends of the filament 990 may be held at a DC voltage, e.g., 0-15 volts with respect to ground. Application of the DC voltage causes the filaments to heat to a very high temperature. When the temperature is sufficiently high, electrons are released (e-beam) from the filaments. A single one of the N cathode materials 990 produces an electron beam (e-beam) that is then focused onto a section of the anode assembly 960. The linear x-ray tube 900 may utilize an array of N (N≥1) cathodes (i.e., the N cathode materials 990) linearly arranged in order to produce multiple electron beams (e-beams), which impact the anode 960 in different sections along the length of the anode assembly 960. The N cathode materials 990 may be connected to one or more high voltage feed-throughs 920 that transfer a voltage from outside the linear x-ray tube 900 to the filaments inside the linear x-ray tube 900. As illustrated in FIGS. 9-10, a linear x-ray tube 900 having N x-ray sources 910, 911, 912, 913 may separately control activation and deactivation of each of the N x-ray sources by connecting each of the N cathode filaments 990 to a separate feed-through 920.

Figure 11:
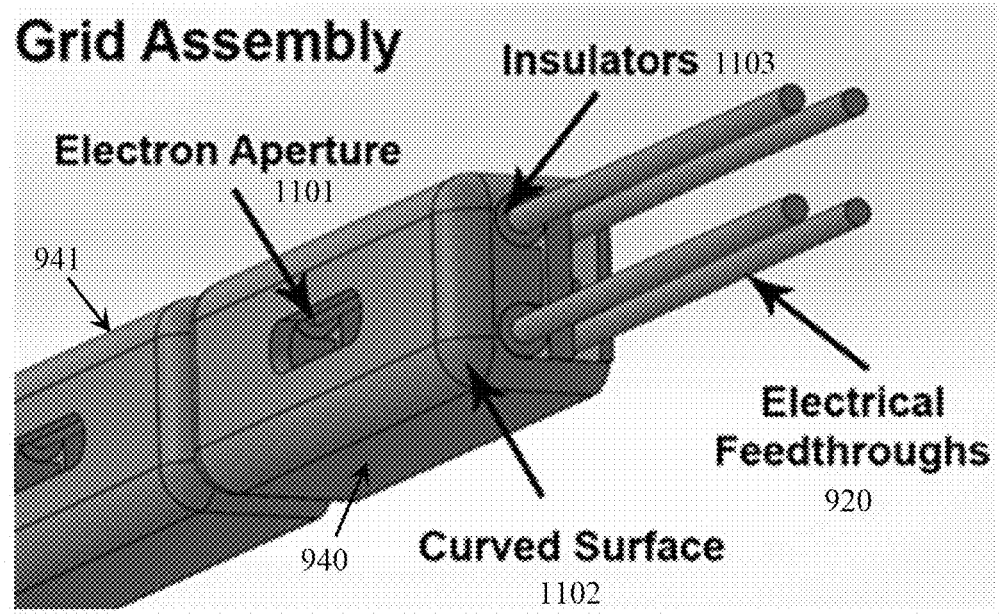
Figure 12:
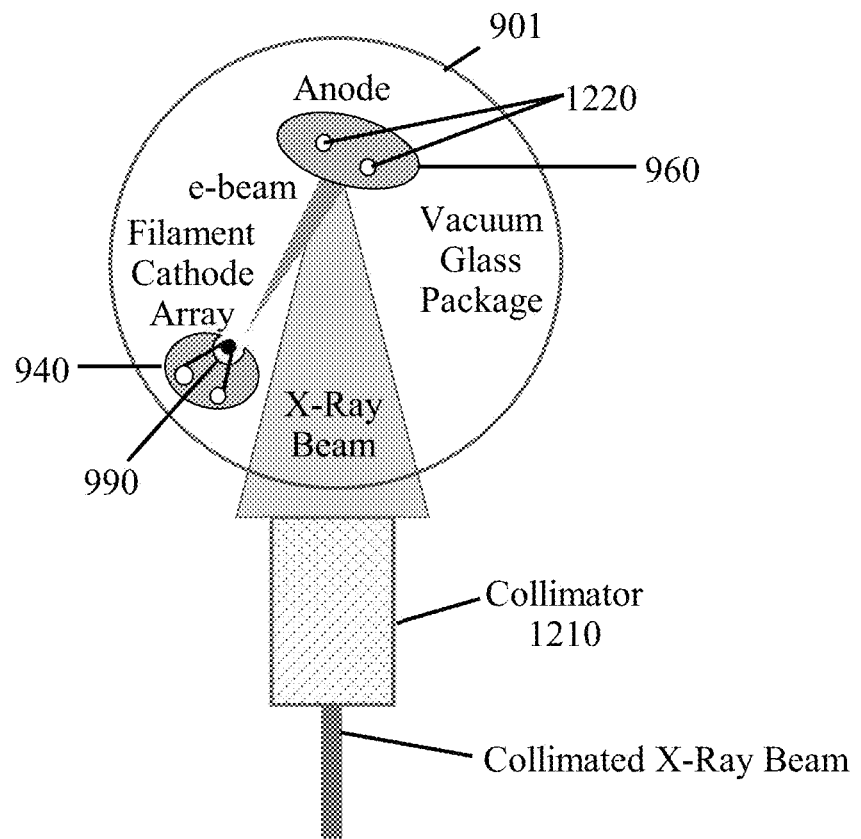

Each grid 940, 941, 942, 943 within the grid assembly 939 may be a conductive (e.g., copper) block, which functions to isolate each of the N electron beams (e-beams) along specific paths inside the x-ray tube 900. Without the grid, electrons might scatter all around inside the x-ray tube 900 causing arcing and/or premature failure of the x-ray tube 900. The electrons that are not emitted along the intended path towards the anode 960 are collected into the grid assembly where there are electrically removed through the grid circuit. Referring to FIGS. 10-12, each of the grids 940, 941, 942, 943 may be configured to hold a voltage used to control the flow of electrons through an aperture 1101 in the grid. Changing the voltage from a negative value to a relatively more positive value will focus the e-beam to a desired shape as the e-beam travels to the anode 960. Each grid may also be shaped to have curved surfaces 1102, which function to generate a uniform electric field distribution in order to mitigate high voltage stress, thus helping to prevent arcs and premature failure of the x-ray tube 900. Each grid may also have a multitude of feed-throughs to allow conducive rods (e.g., copper) of differing voltages to pass through the grid assembly 939. Insulators 1103 (e.g., made of a ceramic) may be clamped to each grid to insulate these copper rods. The entire grid assembly 939 may be demountable, allowing the change of a filament 990 when it needs to be replaced.

Insulators (e.g., made of a ceramic) 971, 972, 973, 974, 975 may be used as high-voltage standoffs. These standoffs 971, 972, 973, 974, 975 may be spaced in between the grids 940 . . . 943 and in between the anode assembly 960 and cathode assembly 939. The insulators 971, 972, 973, 974, 975 may be utilized to mechanically hold the anode assembly 960 in place, and also serve to separate the high voltage from the low voltages. These insulators 971, 972, 973, 974, 975 may also have special cutouts (not shown) to increase the rate of vacuum conduction within the tube package.

A demountable vacuum package configured for implementing a linear x-ray source may include a glass tube 901, O-rings, flanges 902, 903, a gated vacuum valve 922, a turbo pump (not shown), and a rough pump (not shown). The rough pump and turbo pump pull a vacuum on the tube to a high vacuum. The long glass tube 901 holds the x-ray components. The vacuum package 901 may be demountable (e.g., by removing one of the flanges 902, 903) to allow x-ray tube components to be replaced (e.g., when they have reached their end of life). The flanges and O-rings may be used to create a reusable vacuum seal.

The linear x-ray tube 900 may include an integrated cooling system (e.g., water) (not shown). For example, water may be passed through a feed-through 1220 into the vacuum package 901 and into a cavity within the anode 960. There may be also a water feed-through (not shown) for water cooling into the grid assembly to cool the cathodes.

As shown in FIG. 12, the linear x-ray tube 901 may further include a collimator 1210 associated with each of the x-ray sources. The collimator 1210 may have an aperture that is aimed at a detection area where a particular metal alloy scrap piece is to be irradiated. As used herein, a "collimator" is a device having an aperture that limits the transmission of x-rays of an x-ray beam such that the x-rays move in the same, or nearly the same, direction. Within embodiments of the present invention, such collimators may be made from a series of closely spaced parallel metal plates utilized to direct the x-ray beam. X-ray optics (not shown) may be used to focus a divergent primary x-ray beam into a convergent beam. X-ray optics may take the forms of crystals, capillaries, plastics, metals, or glass. The effect of the optics may reduce the amount of power needed by the x-ray tube.

Figure 13:
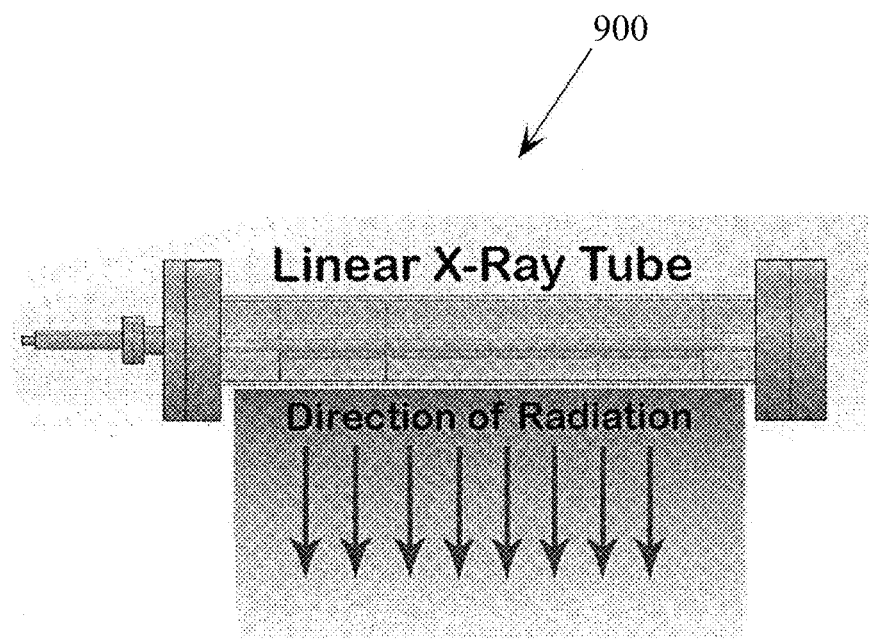

As depicted in FIG. 13, the linear x-ray tube 900 delivers a linear radiation flux outside of the tube 901, which can then be utilized to irradiate along a line in both the x and/or y directions of a plane perpendicular to the direction of the beam. Conventional x-ray sources have one spot on their anode that coincides with the electron beam size. The linear x-ray tube 900 is distinguished from a traditional x-ray source by having the ability to generate radiation in a linear and not a conical fashion, including the use of a collimator to generate an x-ray beam towards a detector(s) having such x and y components. The generation of x-ray flux is dependent on the electron beam spot size. The linear x-ray tube 900 in accordance with aspects of the present disclosure has N electron beam spots arranged in a linear array, and therefore produces a directed x-ray flux with a linear component.

Figure 14:
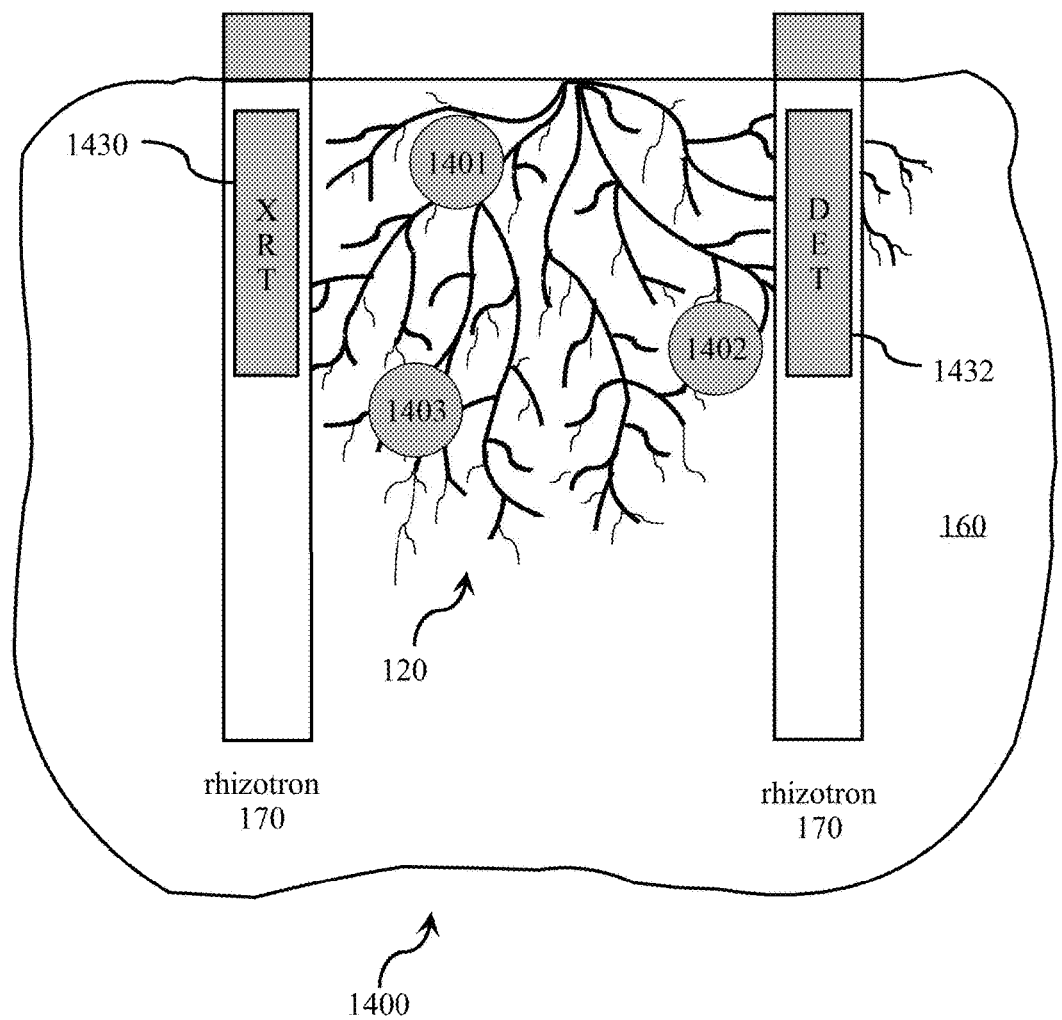
FIG. 14 illustrates a system 1400 with an x-ray tube and detector, configured in accordance with embodiments of the present invention, utilized to generate x-ray fluorescence in plant roots, which may be used to determine the chemical composition of the roots.

FIG. 14 illustrates how an x-ray source 1430 may be utilized to generate fluorescence in a plant root system 120, which may be used to determine the chemical composition of the plant roots at specified locations (e.g., roots 1401, 1402, 1403, etc.) in the soil 160. For the chemical analysis, a single, or multiple, point source tube 1430 may be utilized (which may still be a long tube to match with a rhizotron 170). A detector array 1432, which may also be directly inserted into the soil 160 or a rhizotron 170, may include one or more detectors for detecting x-ray fluorescence emitted from materials in the soil 160 and elements composing the roots 120. The one or more detectors and the associated detector electronics (e.g., the imaging electronics 140) capture this received XRF spectrum to perform signal processing thereon and produce digitized information representing the captured XRF spectrum. Within x-ray fluorescence spectroscopy, the use of characteristic x-rays emitted under excitation provides a method for identification of elements and their relative amounts present in different materials. These x-rays cause each piece of material to fluoresce x-rays at various energy levels, depending on the elements contained in the piece. The energy of emitted x-rays depends on the atomic number of the fluorescing elements.

Signals representing the detected XFR spectrum may be converted into a discrete energy histogram such as on a per-channel (i.e., element) basis. Such a conversion process may be implemented within the imaging electronics 140, or the computer system 150. Within embodiments of the present invention, such imaging electronics 140 or computer system 150 may include a commercially available spectrum acquisition module, such as the commercially available Amptech MCA 5000 acquisition card and software programmed to operate the card. Such a spectrum acquisition module, or other software implemented within the computer system 150 may be configured to implement a plurality of channels for dispersing x-rays into a discrete energy spectrum (i.e., histogram) with such a plurality of energy levels, whereby each energy level corresponds to an element that the one or more detectors have been configured to detect.

The system 100 may be configured so that there are sufficient channels corresponding to certain elements within the chemical periodic table, which are important for distinguishing between different elements typically found within plant root systems and/or surrounding soil. The energy counts for each energy level may be stored in a separate collection storage register. The system then reads each collection register to determine the number of counts for each energy level during the collection interval, and build the energy histogram, which is then used to identify the various elements of the plant root system and/or soil.

Within the detector electronics, a wavelength dispersive x-ray fluorescence ("WD-XRF") analysis or an energy dispersive x-ray fluorescence ("ED-XRF") analysis may be utilized. WD-XRF can be used to simultaneously determine the elemental concentrations of a sample. WD-XRF detectors use crystals and Bragg diffraction to split the fluorescence radiation from the sample into different paths. The location for each path is determined by the energy of fluorescence. Because the fluorescence is split into a fan beam where each location on the beam corresponds to a unique energy level, low cost detectors can be used to detect this location dependent fluorescence. For example, a linear array of a pulse counter, SiPN, or MPPC detector(s) could be used instead of SDD, SiLi, or Ge detectors. The use of pulse counters or SiPN diodes are less expensive and bring down the overall cost of the detection system. WD-XRF differs from energy dispersive x-ray fluorescence ("ED-XRF") analysis by the use of the detectors. ED-XRF systems use a single detector operating in an energy dispersive mode. ED detectors, such as the SiLi and SDD, detect all energies of the fluorescent radiation and then electronically separate them all into bins in order to generate the spectrum.

Figure 15:
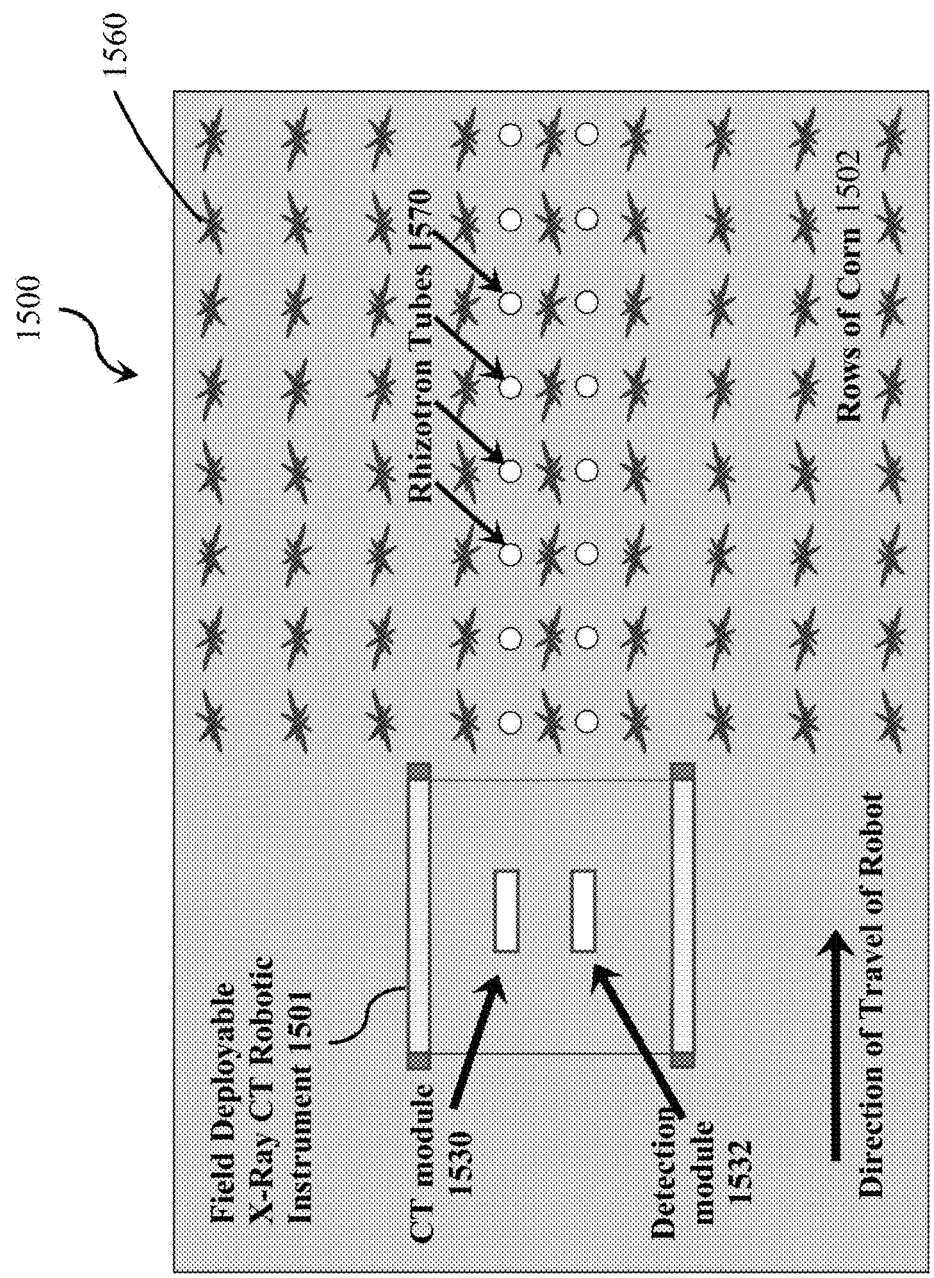
FIG. 15 illustrates embodiments of the present invention configured for performing x-ray imaging and/or chemical analysis of plant roots in the field.

FIG. 15 illustrates embodiments of the present invention in which a system 1500 is utilized in the field for performing x-ray imaging of root systems of a plurality of plants. In a non-limiting example, the system 1500 may be implemented in an already planted agricultural field whereby a plurality of plants 1502 (e.g., rows of corn plants) are then analyzed in order to perform x-ray imaging of the root systems of such multiple plants. Within such an agricultural field, a plurality of rhizotrons 1570 may be inserted into the native soil 1560 surrounding multiple plants 1502.

In the top-down view of the schematic of the system 1500, some sort of moveable platform 1501 may include all or portions of an x-ray imaging system (e.g., the plant root characterization system 100), which may include an x-ray CT module 1530 and a detector module 1532. The x-ray CT module 1530 may include at least one linear x-ray tube (e.g., an x-ray tube 130), while the detector module 1532 may include at least one detector array (e.g., a detector array 132).

The moveable platform 1501 may have any suitable mechanism for moving the platform 1501 along one or more rows of the plants planted within an agriculture field. Such movement may be performed manually, or the platform 1501 may be motorized, including being controlled by a robotic mechanism configured to position the platform 1501 at desired locations along the one or more rows of plants. Then, the platform 1501 may be positioned relative to one or more plants 1502 so that at least one linear x-ray tube 130 can be inserted into at least one rhizotron 1570. In a similar manner, at least one of the detector arrays 132 can be inserted into one or more of the rhizotrons 1570. Alternatively, well-known imaging technology may be utilized with a well-known robotic mechanism for systematically positioning the platform 1501 at sequential locations along the one or more rows of plants 1502 whereby the robotic mechanism then automatically inserts a linear x-ray tube(s) 130 and detector array(s) 132 into various rhizotrons 1570 to perform the x-ray imaging of the root system(s) of plants 1502. The moveable platform may be configured with a clearance height and a distance between its wheels so that it can be moved along planted rows of plants in the field so as to not damage the plants. In other words, as is well-known in agriculture, the platform height may be sufficient (and also possibly adjustable) to clear the tops of the plants as it moves down a row of plants. Furthermore, the distance between the wheels of the platform may be configured so that the wheels roll on the surface of the field in locations between the rows of plants.

Exemplary detectors that may be utilized in embodiments of the present invention may be commercially obtained from Hamamatsu Photonics K.K. for the 2D imaging detectors (e.g., for the detectors in the detector arrays 132), and from AMPTEK or Ketek for the chemical analysis (e.g., for the detectors in the detector array 1432). For example, the detectors utilized may be Si-PIN X-Ray Detectors from MOXTEK, Inc., XR-100CR Si-PIN X-Ray Detector from Amptek, Inc., or VITUS Silicon Drift Detector (SDD) from KETEK GmbH.

Figure 16:
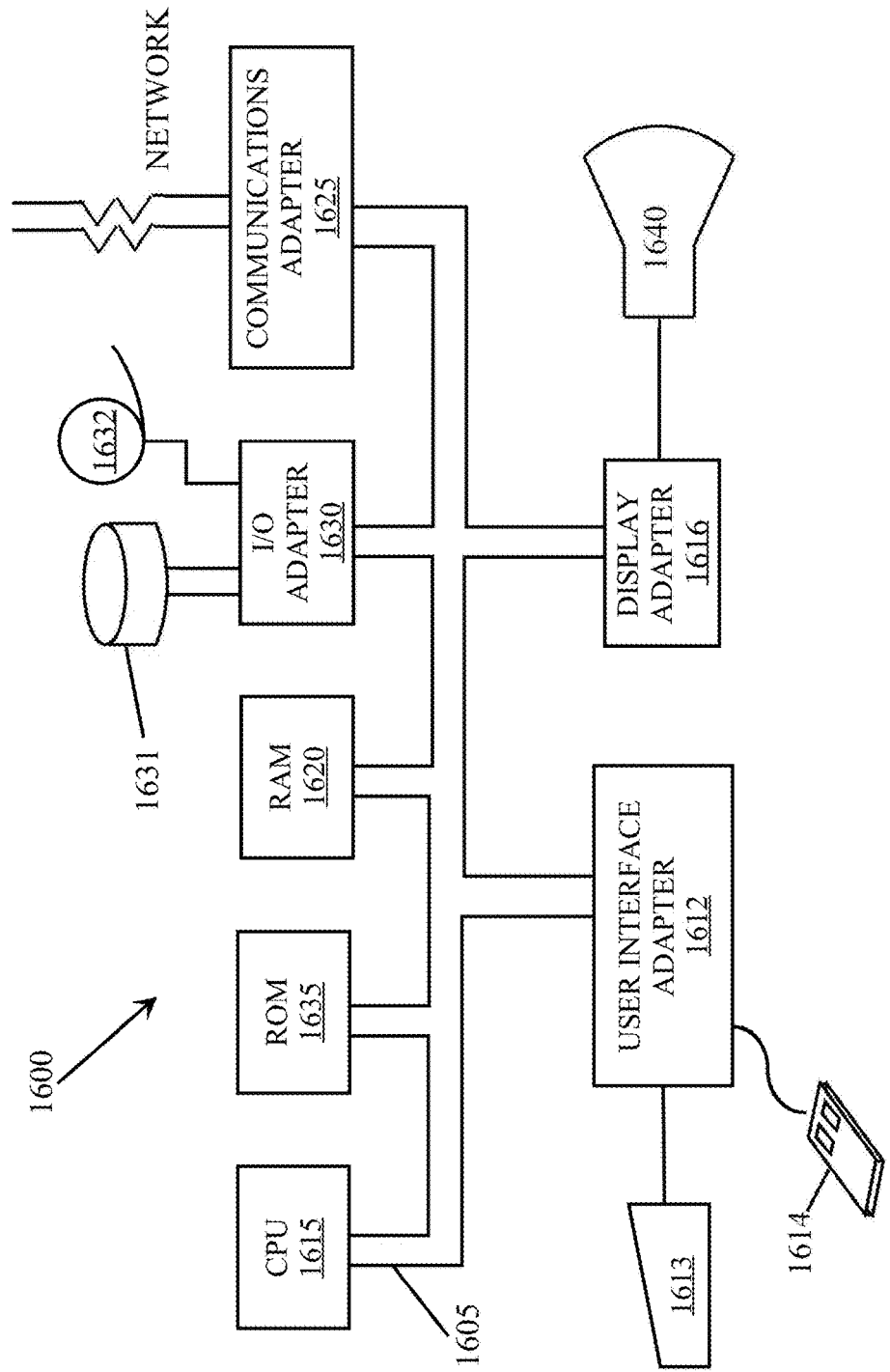
FIG. 16 illustrates a block diagram of a data processing system configured in accordance with embodiments of the present invention.

With reference now to FIG. 16, a block diagram illustrating a data processing ("computer") system 1600 is depicted in which aspects of embodiments of the invention may be implemented. The image processing system 150 of FIG. 1 may be implemented within the computer system 1600. The computer system 1600 may employ a peripheral component interconnect ("PCI") local bus architecture. Although the depicted example employs a PCI bus, other bus architectures such as Accelerated Graphics Port ("AGP") and Industry Standard Architecture ("ISA") may be used, among others. A processor (CPU) 1615, a volatile memory (RAM) 1620, and a non-volatile memory (ROM) 1635 may be connected to a PCI local bus 1605 through a PCI Bridge (not shown). The PCI Bridge also may include an integrated memory controller and cache memory for the processor 1615. Additional connections to the PCI local bus 1605 may be made through direct component interconnection or through add-in boards. In the depicted example, a communication (e.g., network (LAN) adapter 1625, an I/O (e.g., small computer system interface ("SCSI") host bus) adapter 1630, and expansion bus interface (not shown) may be connected to the PCI local bus 1605 by direct component connection. An audio adapter (not shown), a graphics adapter (not shown), and a display adapter 1616 (coupled to a display 1640) may be connected to the PCI local bus 1605 (e.g., by add-in boards inserted into expansion slots).

The user interface adapter 1612 provides a connection for a keyboard 1613 and a mouse 1614, a modem (not shown), and additional memory (not shown). The I/O adapter 1630 provides a connection for a hard disk drive 1631, a tape drive 1632, and a CD-ROM drive (not shown).

An operating system may be run on the processor (CPU) 1615 and used to coordinate and provide control of various components within the computer system 1600. In FIG. 16, the operating system may be a commercially available operating system. An object-oriented programming system such as Java may run in conjunction with the operating system and provide calls to the operating system from Java programs or programs executing on the computer system 1600. Instructions for the operating system, the object-oriented operating system, and programs may be located on the non-volatile memory (ROM) 1635 storage devices, such as the hard disk drive 1631, and may be loaded into the volatile memory (RAM) 1620 for execution by the processor (CPU) 1615.

Those of ordinary skill in the art will appreciate that the hardware in FIG. 16 may vary depending on the implementation. Other internal hardware or peripheral devices, such as a flash ROM (or equivalent nonvolatile memory) or optical disk drives and the like, may be used in addition to or in place of the hardware depicted in FIG. 16. Also, the processes of the present invention may be applied to a multi-processor computer system.

As another example, the computer system 1600 may be a stand-alone system configured to be bootable without relying on some type of network communication interface, whether or not the computer system 1600 includes some type of network communication interface. As a further example, the computer system 1600 may be an embedded controller, which is configured with a ROM and/or flash ROM providing a non-volatile memory storing operating system files or user-generated data.

The depicted example in FIG. 16 and above-described examples are not meant to imply architectural limitations. Further, a computer program form of the present invention may reside on any computer readable storage medium (i.e., floppy disk, compact disk, hard disk, tape drive, ROM, RAM, etc.) used by the computer system 1600. (The terms "computer," "system," "computer system," and "data processing system" may be used interchangeably herein.)

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

All publications and patent applications are herein incorporated by reference to the same extent as if each individual publication or patent application was specifically and individually indicated to be incorporated by reference.

The singular forms "a," "an," and "the" include plural referents unless the context clearly dictates otherwise. As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a defacto equivalent of any other member of the same list solely based on their presentation in a common group without indications to the contrary.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material, or acts that support the means-plus function are expressly recited in the description herein. Accordingly, the scope of the invention should be determined solely by the appended claims and their legal equivalents, rather than by the descriptions and examples given herein.

What is claimed is:

1. A system comprising:
    a linear x-ray tube comprising a plurality of individually controllable x-ray sources linearly aligned adjacent to each other within the linear x-ray tube;
    an x-ray detector array comprising a plurality of x-ray detectors; and
    an x-ray computed tomography ("CT") imaging system coupled to the linear x-ray tube and the x-ray detector array, wherein the x-ray CT imaging system is configured to receive from the plurality of x-ray detectors information pertaining to detected x-rays emitted through a plant root system, wherein the x-ray CT imaging system further comprises a software program configured to output CT images of the plant root system imaged by operation of the linear x-ray tube and the x-ray detector array.

2. The system as recited in claim 1, wherein the plurality of x-ray detectors are linearly aligned within the x-ray detector array.

3. The system as recited in claim 1, wherein the linear x-ray tube is configured to fit within a rhizotron.

4. The system as recited in claim 3, further comprising a moveable platform configured with a platform height sufficient to clear tops of plants having plant root systems as the moveable platform moves down rows of said plants planted within an agriculture field, wherein the linear x-ray tube, the x-ray detector array, and the x-ray CT imaging system are mounted on the moveable platform, and wherein the moveable platform comprises wheels configured so that the wheels roll on a surface of the agricultural field in locations between the rows of said plants.

5. The system as recited in claim 4, further comprising:
    a first rhizotron configured to be inserted within soil of the agriculture field in proximity to the plant root systems, wherein the linear x-ray tube is configured to fit within the first rhizotron; and
    a second rhizotron configured to be inserted within the soil of the agriculture field in proximity to the plant root systems, wherein the x-ray detector array is configured to fit within the second rhizotron.

6. The system as recited in claim 1, further comprising:
    a first rhizotron configured to be inserted within soil in proximity to the plant root system, wherein the linear x-ray tube is configured to fit within the first rhizotron; and
    a second rhizotron configured to be inserted within the soil in proximity to the plant root system, wherein the x-ray detector array is configured to fit within the second rhizotron.

7. The system as recited in claim 6, further comprising:
    a third rhizotron configured to be inserted within the soil in proximity to the plant root system; and
    another x-ray detector array configured to fit within the third rhizotron, and wherein both the x-ray detector array and the another x-ray detector array are configured to detect x-rays emitted by the linear x-ray tube through the soil and the plant root system.

8. The system as recited in claim 6, further comprising:
    a third rhizotron configured to be inserted within the soil in proximity to the plant root system; and
    another x-ray detector array configured to fit within the third rhizotron;

a fourth rhizotron configured to be inserted within the soil in proximity to the plant root system; and another linear x-ray tube configured to fit within the fourth rhizotron, and wherein the x-ray detector array and the another x-ray detector array are configured to detect x-rays emitted by either the linear x-ray tube or the another linear x-ray tube through the soil and the plant root system.

9. The system as recited in claim 1, wherein the linear x-ray tube comprises:

a first one of the plurality of individually controllable x-ray sources comprising a first grid assembly and a first cathode having a first electron emitter positioned within the first grid assembly;

a second one of the plurality of individually controllable x-ray sources comprising a second grid assembly and a second cathode having a second electron emitter positioned within the second grid assembly, wherein the first grid assembly and the second grid assembly are linearly aligned with each other within the linear x-ray tube;

an anode bar aligned in parallel to the first grid assembly and the second grid assembly, wherein the first electron emitter and the second electron emitter are physically separated from each other so that the first electron emitter and the second electron emitter are operable to separately emit electrons towards separate portions of the anode bar;

one or more insulator spacers configured to position the anode bar a predetermined distance from each of the first grid assembly and the second grid assembly;

a first electrical feed-through configured to provide a first voltage potential to the anode bar;

a second electrical feed-through configured to provide a second voltage potential to the first cathode; and a third electrical feed-through configured to provide a third voltage potential to the second cathode, wherein the second voltage potential and the third voltage potential are configured to be separately controllable.

10. A method for characterizing a plant root system growing within a native soil, the method comprising:

positioning a first linear x-ray tube within a first rhizotron inserted within the native soil;

positioning a first x-ray detector array within a second rhizotron inserted within the native soil, wherein the first x-ray detector array includes one or more x-ray detectors;

activating a first x-ray source within the first linear x-ray tube so that the first x-ray source emits first x-rays through the native soil and a first portion of the plant root system;

detecting the first x-rays after the first x-rays have passed through the native soil and the first portion of the plant root system with at least one of the one or more x-ray detectors of the first x-ray detector array; and processing the detected first x-rays for characterizing physical properties of the plant root system.

11. The method as recited in claim 10, further comprising:

positioning a second x-ray detector array within a third rhizotron inserted within the native soil, wherein the second x-ray detector array includes one or more x-ray detectors;

activating the first x-ray source within the first linear x-ray tube so that the first x-ray source emits second x-rays through the native soil and a second portion of the plant root system;

detecting the second x-rays after the second x-rays have passed through the native soil and the second portion of the plant root system with at least one of the one or more x-ray detectors of the second x-ray detector array; and processing the detected second x-rays for characterizing physical properties of the plant root system.

12. The method as recited in claim 10, further comprising:

positioning a second linear x-ray tube within a third rhizotron inserted within the native soil;

positioning a second x-ray detector array within a fourth rhizotron inserted within the native soil, wherein the second x-ray detector array includes one or more x-ray detectors;

activating a second x-ray source within the second linear x-ray tube so that the second x-ray source emits second x-rays through the native soil and a second portion of the plant root system;

detecting the second x-rays after the second x-rays have passed through the native soil and the second portion of the plant root system with at least one of the one or more x-ray detectors of the second x-ray detector array; and processing the detected second x-rays for characterizing physical properties of the plant root system.

13. The method as recited in claim 10, further comprising:

activating a second x-ray source within the first linear x-ray tube so that the second x-ray source emits second x-rays through the native soil and a second portion of the plant root system;

detecting the second x-rays after the second x-rays have passed through the native soil and the second portion of the plant root system with at least one of the one or more x-ray detectors of the first x-ray detector array; and processing the detected second x-rays for characterizing physical properties of the plant root system.

14. The method as recited in claim 10, wherein the processing the detected first x-rays for characterizing physical properties of the plant root system comprises outputting CT images of the plant root system as a function of the detected first x-rays by a CT imaging system.

15. The method as recited in claim 10, wherein the processing the detected first x-rays for characterizing physical properties of the plant root system comprises analyzing an x-ray fluorescence spectrum detected by the at least one of the one or more x-ray detectors of the first x-ray detector array to identify elements within the plant root system.

16. The method as recited in claim 10, wherein the first rhizotron and the second rhizotron are inserted within the native soil located within an agriculture field containing a plurality of plants each having a plant root system.

17. A method for characterizing a plant root system growing within soil, the method comprising:

positioning a linear x-ray tube within the soil, wherein the linear x-ray tube comprises a plurality of individually controllable x-ray sources linearly aligned adjacent to each other within the linear x-ray tube;

positioning an x-ray detector array within the soil, wherein the x-ray detector array comprises a plurality of x-ray detectors;

activating a first one of the plurality of individually controllable x-ray sources within the linear x-ray tube so that the first one of the plurality of individually controllable x-ray sources emits first x-rays through the soil and a first portion of the plant root system;

detecting the first x-rays after the first x-rays have passed through the soil and the first portion of the plant root system with at least one of the plurality of x-ray detectors of the x-ray detector array;

activating a second one of the plurality of individually controllable x-ray sources within the linear x-ray tube so that the second one of the plurality of individually controllable x-ray sources emits second x-rays through the soil and a second portion of the plant root system;

detecting the second x-rays after the second x-rays have passed through the soil and the second portion of the plant root system with at least one of the plurality of x-ray detectors of the x-ray detector array; and processing the detected first x-rays and the detected second x-rays for characterizing physical properties of the plant root system.

18. The method as recited in claim 17, wherein the activating the second one of the plurality of individually controllable x-ray sources within the linear x-ray tube comprises activating the second one of the plurality of individually controllable x-ray sources subsequent to deactivating of the first one of the plurality of individually controllable x-ray sources within the linear x-ray tube.

19. The method as recited in claim 17, wherein the processing the detected first x-rays and the detected second x-rays for characterizing physical properties of the plant root system comprises outputting CT images of the plant root system as a function of the detected first x-rays and the detected second x-rays.

20. The method as recited in claim 17, wherein the linear x-ray tube comprises:

the first one of the plurality of individually controllable x-ray sources comprising a first grid assembly and a first cathode having a first electron emitter positioned within the first grid assembly;

the second one of the plurality of individually controllable x-ray sources comprising a second grid assembly and a second cathode having a second electron emitter positioned within the second grid assembly, wherein the first grid assembly and the second grid assembly are linearly aligned with each other within the linear x-ray tube;

an anode bar aligned in parallel to the first grid assembly and the second grid assembly, wherein the first electron emitter and the second electron emitter are physically separated from each other so that the first electron emitter and the second electron emitter are operable to separately emit electrons towards separate portions of the anode bar;

one or more insulator spacers configured to position the anode bar a predetermined distance from each of the first grid assembly and the second grid assembly;

a first electrical feed-through configured to provide a first voltage potential to the anode bar;

a second electrical feed-through configured to provide a second voltage potential to the first cathode; and a third electrical feed-through configured to provide a third voltage potential to the second cathode, wherein the second voltage potential and the third voltage potential are configured to be separately controllable.

\* \* \* \* \*